United States Patent [19]
Zinnanti

[11] Patent Number: 5,348,555
[45] Date of Patent: Sep. 20, 1994

[54] ENDOSCOPIC SUCTION, IRRIGATION AND CAUTERY INSTRUMENT

[76] Inventor: William J. Zinnanti, 2508 Vista Wood Cir. No. 36, Thousands Oaks, Calif. 91362

[21] Appl. No.: 51,546

[22] Filed: Apr. 26, 1993

[51] Int. Cl.$^5$ ............................................. A61B 17/39
[52] U.S. Cl. ....................................... 606/49; 604/33; 604/21; 606/45; 606/29
[58] Field of Search ......................... 606/27, 45, 46, 28, 606/32, 33, 40, 41, 47, 48; 604/33, 35, 21

[56] References Cited

U.S. PATENT DOCUMENTS

| | | | |
|---|---|---|---|
| 2,669,223 | 2/1954 | Friend | 604/33 |
| 3,835,842 | 9/1974 | Iglesias | 606/46 X |
| 4,451,257 | 5/1984 | Atchley | 604/33 X |
| 5,163,926 | 11/1992 | Bailey et al. | 604/35 X |
| 5,186,714 | 2/1993 | Boudreault et al. | 604/33 X |
| 5,188,591 | 2/1993 | Dorsey, III | 604/33 |
| 5,190,541 | 3/1993 | Abele et al. | 604/35 X |
| 5,195,958 | 3/1993 | Phillips | 604/33 |

*Primary Examiner*—Peter A. Aschenbrenner
*Attorney, Agent, or Firm*—Allen A. Dicke, Jr.

[57] ABSTRACT

The irrigator aspirator instrument body has finger-operated valves for respective connection to sources of suction and irrigation. The body has connection ports on each end that it is reversible and has a clear polymer cannula attached in one of the ports for endoscopic utilization. The body is also transparent so that, during suction, complete aspiration can be observed. The other port carries a cautery rod which can be extended out of the cannula. The polymer cannula prevents capacitive charge coupling to the cannula.

23 Claims, 4 Drawing Sheets

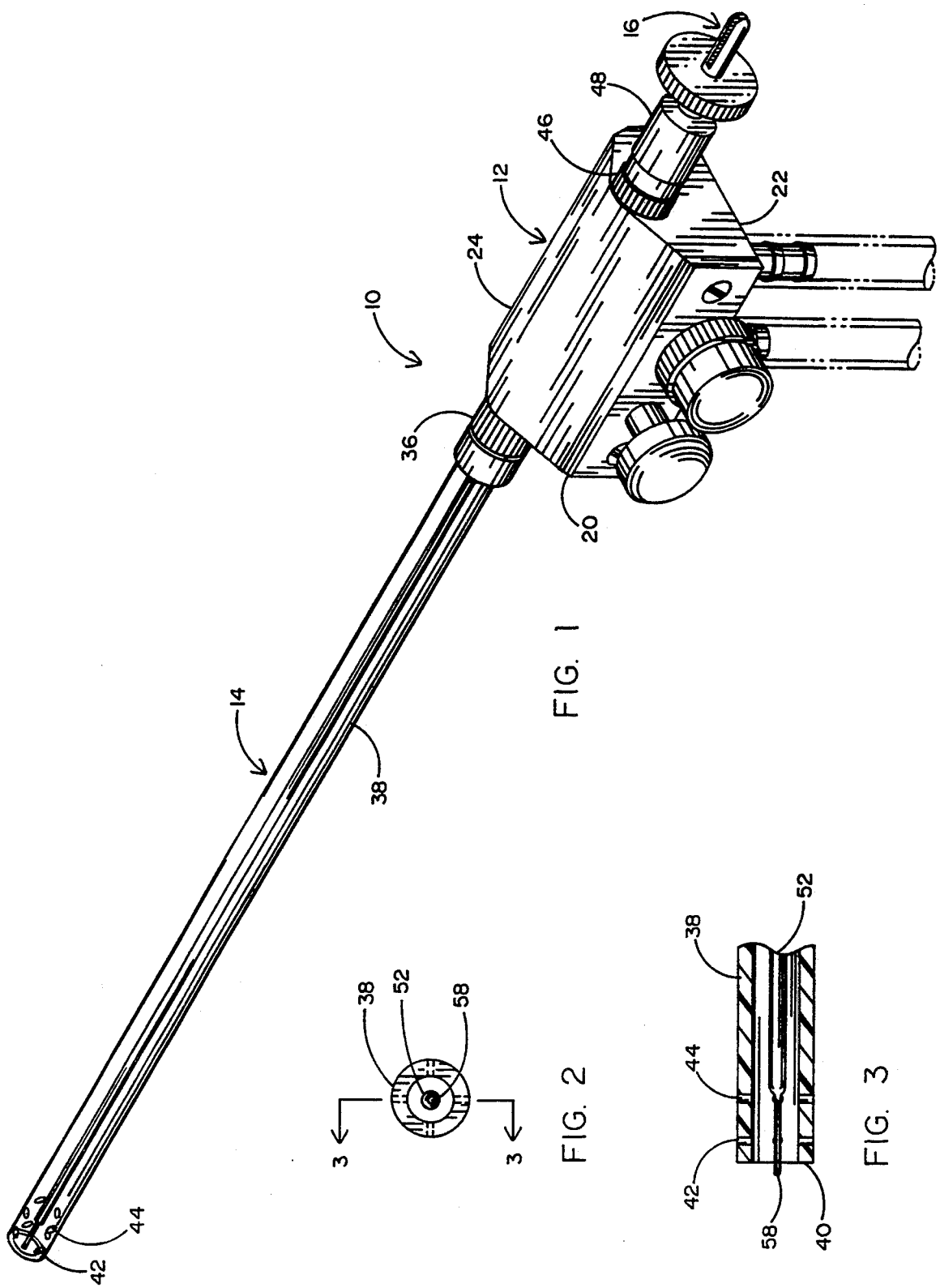

ENDOSCOPIC SUCTION, IRRIGATION AND CAUTERY INSTRUMENT

FIELD OF THE INVENTION

This invention is in the field of endoscopic medical instruments which are used through an abdominal (or other) port: to perform suction, irrigation and cautery functions within the body.

BACKGROUND OF THE INVENTION

Modern advances in surgical techniques have resulted in laparoscopic surgery. The patient is grounded; a plastic or metal trocar port is placed in the abdominal wall; and the abdomen is distended by insufflation of carbon dioxide. This is done to open up the space between the organs where the endoscope and the laparoscopic instruments are manipulated.. The common cannula through which the cautery electrode is passed is made of metal. Even though the electrode is electrically insulated, an electrical charge is capacitively coupled to the metal cannula. The metal cannula is not grounded, but the patient's body is grounded for monopolar cautery technique. When a cautery charge is applied through the cautery electrode, a capacitively coupled charge is created in the metal cannula. When the metal cannula is touching tissue inside the abdominal cavity, the capacity coupled charge can cause the metal cannula to burn tissue with which it is in contact. Since this burn is in an area unexpected by the surgeon, often it goes undetected. This is one of the major causes of post-surgery morbidity and infection resulting from laparoscopic surgery. Thus, there is need for improvement in endoscopic cautery instruments.

SUMMARY OF THE INVENTION

In order to aid in the understanding of this invention, it can be stated in essentially summary form that it is directed to an endoscopic suction, irrigation and cautery instrument wherein the valve body and the cannula are made of clear polymer material so that suction results can be observed. The body is the same on both ends so that the cannula can be attached at either end. The opposite end carries a cautery electrode in the form of a rod which extends to the open tip end of the cannula. The cautery electrode can be manipulated to be exposed or retracted. The body has valves which can be digitally operated and connected to suction or irrigation so that either can be achieved by the surgeon. At least the suction valve has an adjustable stop thereon to control its opening to control the application of vacuum at the open end of the lumen.

It is, thus, an object and advantage of this invention to provide an endoscopic suction, irrigation and cautery instrument which can be manipulated to perform its suction, irrigation or cautery functions in laparoscopic surgery, including utilization of a dielectric lumen to avoid capacitive charge coupling to the lumen.

It is another object and advantage of this invention to provide an endoscopic suction instrument which has a transparent lumen and transparent valve body so that the progress of suction material can be observed.

It is a further object and advantage of this invention to provide an endoscopic suction instrument for laparoscopic surgery which has an adjustable stop on the valve body held by the surgeon that the surgeon can control the amount of vacuum flow during use.

It is another object and advantage of this invention to provide an endoscopic suction, irrigation and cautery instrument which is arranged so that it can be assembled for either right-hand or left-hand use.

It is a further object and advantage of this invention to provide an endoscopic suction instrument which is provided with interchangeable clear polymer lumens of different sizes so that large material such as blood clots and gallstones can be suctioned away, and a small lumen may be employed for basic suction of minor bleeding and basic irrigation during cautery.

It is another object and advantage of this invention to provide an endoscopic suction, irrigation and cautery instrument wherein the cautery electrode extends through the clear polymer suction and irrigation lumen so that the lumen protects the cautery electrode, with the advance of the cautery electrode being controlled by the surgeon as he holds the body of the instrument.

Other objects and advantages of this invention will become apparent from a study of the following portion of the specification, the claims and the attached drawings.

BRIEF DESCRIPTION OF THE DRAWINGS

FIG. 1 is an isometric view of the endoscopic suction, irrigation and cautery instrument of this invention.

FIG. 2 is an enlarged end-elevational view of the lumen with the cautery electrode therein.

FIG. 3 is a section taken generally along line of FIG. 2, with parts broken away.

DESCRIPTION OF THE PREFERRED EMBODIMENT

Figure 4:
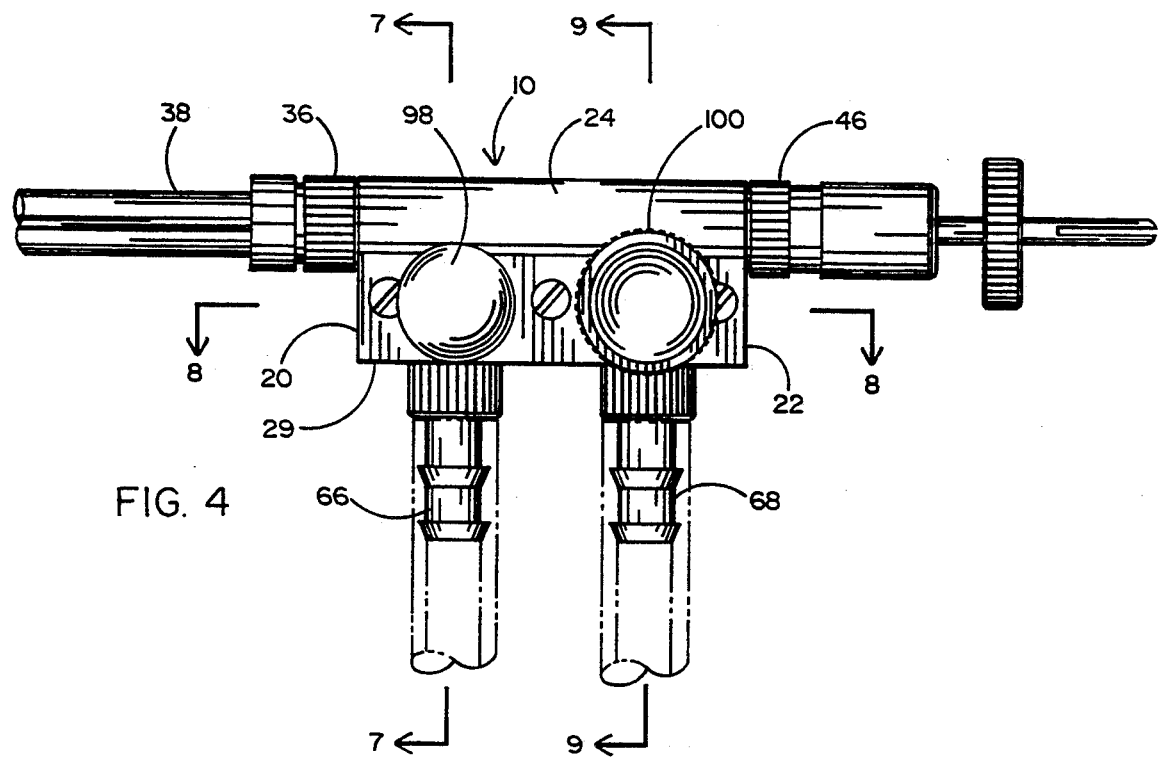
FIG. 4 is a side-elevational view of the instrument, with part of the lumen broken away.
Figure 5:
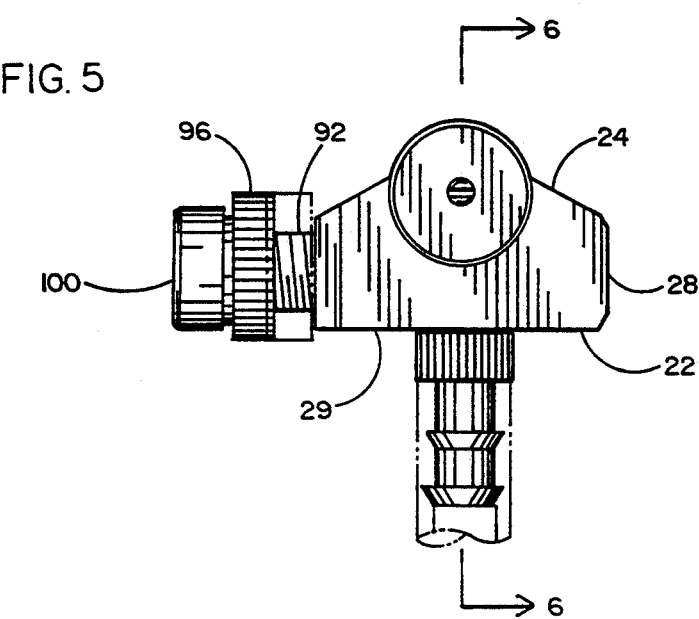
FIG. 5 is a rear-elevational view of the instrument, as seen from the right of FIG. 4.
Figure 6:
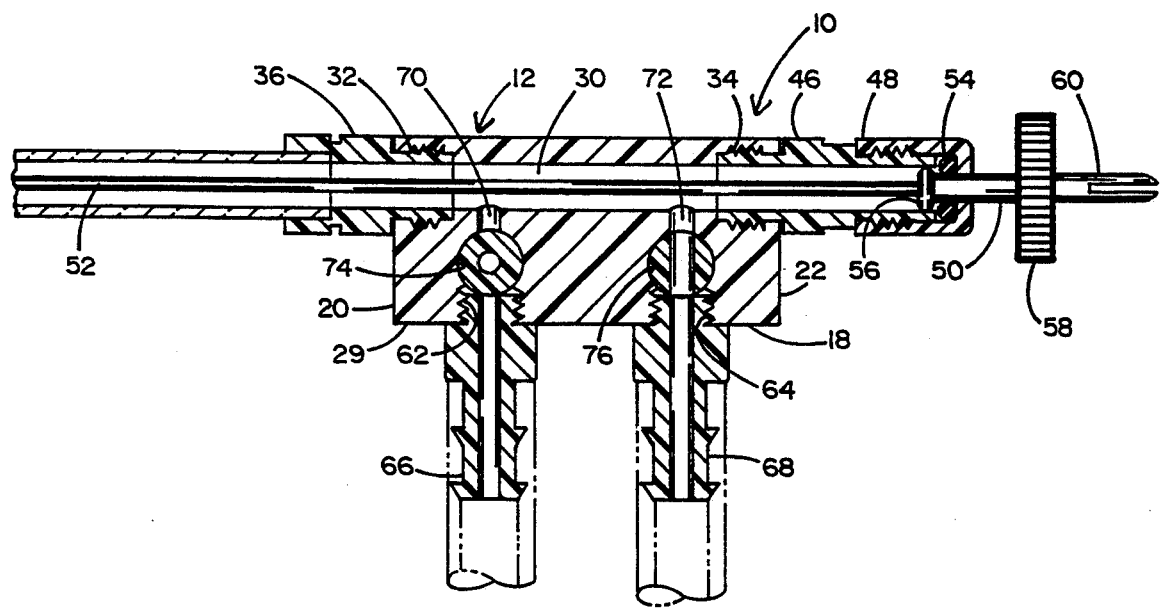
FIG. 6 is a section taken generally along line 6—6 of FIG. 5.

The endoscopic suction, irrigation and cautery instrument of this invention is generally indicated at 10 in FIG. 1. It is also shown in FIGS. 4 and 6 with part of the cannula broken away. The instrument 10 comprises a body 12, cannula 14 and cautery electrode 16. The body 12 is seen in section in FIGS. 6, 7 and 9. The body comprises a block of transparent synthetic polymer composition material. The material must be fairly hard and rigid and must be capable withstanding autoclave sterilization temperatures. Polycarbonate is suitable. The block has ends 20 and 22. The four sides are palm side 24, valve side 26, bottom side 28 and nipple side 29. The sides are generally parallel to each other, except that the palm side is convex. The ends are parallel to each other and generally at right angles to the sides. The body is sized so that it may be engaged in the hand with the bottom against the heel of the hand and the palm side 24 against the surgeon's palm with the surgeon's fingers extending around the valve side.

The block has a main passage through 30 therethrough (see FIGS. 6 and 9) which extends from end to end. At its ends, the main passage 30 has female threaded connection sockets 32 and 34 therein (see FIG.

6). These threaded sockets are identical, but on opposite ends of the body. Tubular fitting 36 has male threads thereon which engage into the socket 32. The tubular fitting is a fitting which carries cannula 38 thereon. The cannula is a clear polymer tube which extends to a face 40. Just behind the face are vent holes 42 and 44 which are vent holes to permit the cannula to pull away even if the face is sucked against some tissue. The cross holes extend all the way across and are also represented by further cross holes at right angles to the axial length of the tubular cannula 38. The cannula 38 can be a throwaway device and, thus, need not be subject to heat sterilization. The cannula 38 may be made of polyvinyl chloride, or similar material, or acrylic type materials. Since the sockets 32 and 34 are the same, the cannula may be installed in either end of the body. In FIG. 1, it can be visualized that the body 12 is grasped in the surgeon's hand with the heel of his hand against side 28, the palm of his hand against side 24, and his fingers available to actuate the valves on the near side. In such a circumstance, the cannula 38 extends substantially parallel to the surgeon's knuckle ridge in a direction away from his thumb. Should the surgeon be left-handed, the cannula can be placed in socket 34 so that the surgeon can grasp the body in his left hand in the same manner as previously described. In that case, the cannula 38 would extend generally parallel to the surgeon's knuckle ridge in the direction away from his thumb.

Cautery fitting 46 screws into the female threaded socket 34, as seen in FIG. 6. Fitting 46 has a male thread on the outer end thereof with cap 48 threaded thereon. The cap has an opening through which the shank 50 of cautery electrode 52 passes. An O-ring 54 engages around the shank 50 and is compressed at the end of fitting 46 to seal the opening and provide frictional resistance of movement of the cautery electrode with respect to the body 12. Cross pin 56 is engaged through the cautery electrode and is positioned on the left side of the O-ring 54, as seen in FIG. 6. This limits the rightward motion of the cautery electrode with its point 58 recessed, as shown in FIG. 3. Adjustment wheel 58 is fixed to the shaft 50. In the right-hand, recessed position of the cautery electrode 52, there is space between the wheel 58 and the cap 48. The adjustment wheel 58 is positioned so that it can be engaged by the thumb to rotate and advance the cautery electrode. The advancement limit is achieved by the adjustment wheel engaging on cap 48. Electrode connector 60 extends to the right of adjustment wheel 58 and is for electrical connection from a conventional cautery machine. Thus, by one-handed operation, the cannula 38 can be positioned and the cautery electrode extended or retracted with respect to the cannula.

Figure 7:
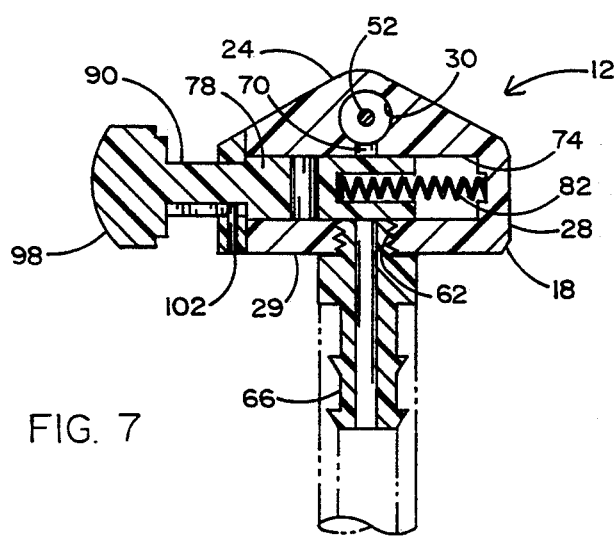
FIG. 7 is a section taken generally along line 7—7 of FIG. 4.
Figure 9:
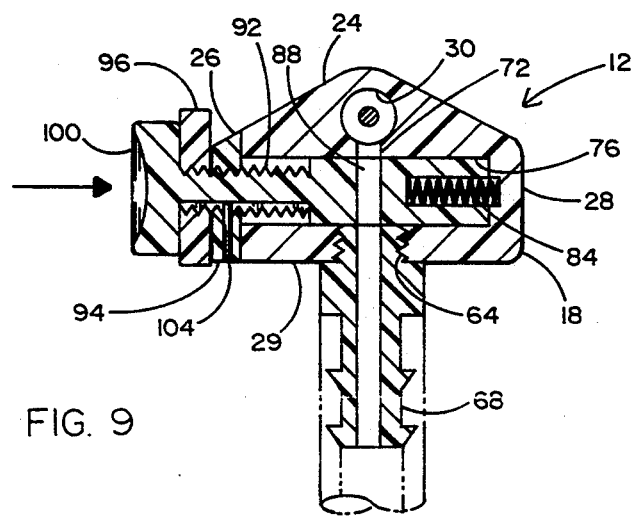
FIG. 9 is a section taken generally along line 9—9 of FIG. 4.

The nipple side 29 of the body has two threaded sockets 62 and 64 into which are respectively threaded nipples 66 and 68, see FIGS. 6, 7 and 9. The nipples are barbed on the exterior to receive a flexible polymer hose. The nipples have openings therethrough for fluid connection with respect to the hose. Hoses are shown in dashed lines in FIGS. 1, 4, 5, 7 and 9. The hose connected to nipple 66 is connected to supply irrigation fluid, such as saline solution. The hose connected to nipple 68 is connected to a source of vacuum. Irrigation passage 70 connects the irrigation tube nipple 66 to the main passage 30, see FIGS. 6 and 7. Similarly, vacuum passage 72 connects vacuum nipple 68 to main passage 30, see FIGS. 6 and 9.

Figure 8:
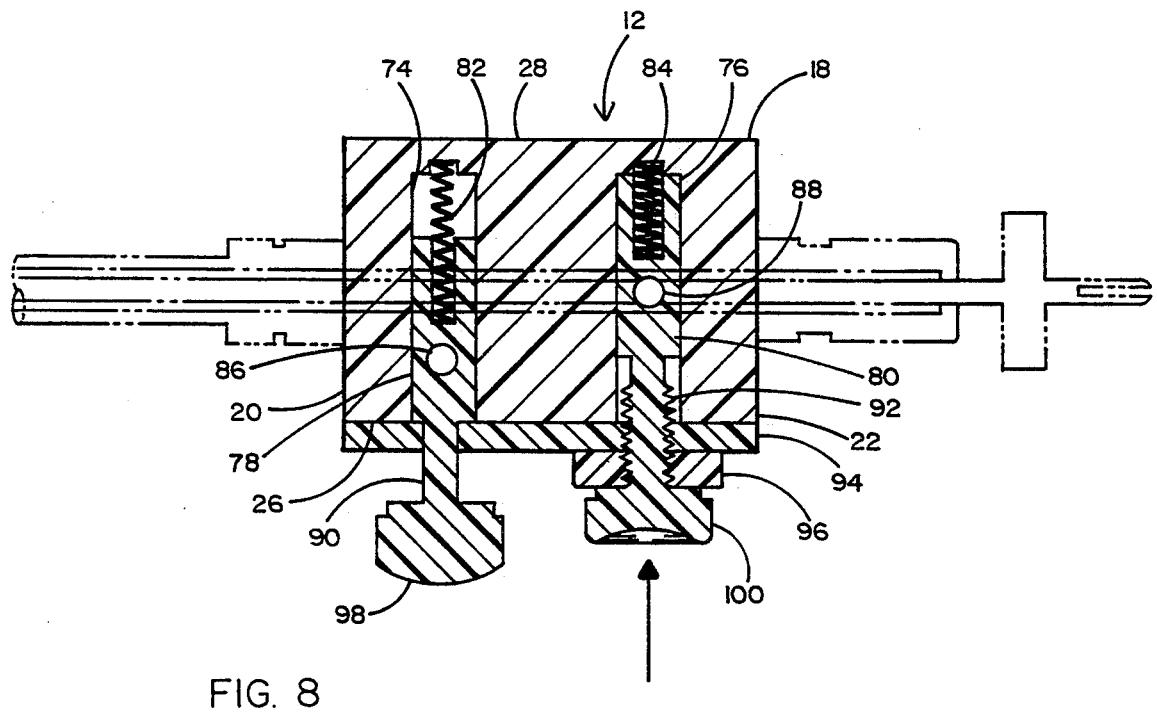
FIG. 8 is a section taken generally along line of FIG. 4.

Valves are connected to control fluid flow. Valve bores 74 and 76 respectively intersect irrigation passage 70 and vacuum passage 72, see FIGS. 6, 7, 8 and 9. As is best seen in FIGS. 7, 8 and 9, slide valves are positioned in these valve bores. Valve plungers 78 and 80 are respectively slidably mounted in bores 74 and 76. Compression springs 82 and 84 are received in spring pockets in the bottom of the plungers and engage against the bottom of the valve bores to urge the valve plungers to the off position, which is shown for valve plunger 78 in FIGS. 7 and 9. The valve plungers have cross bores 86 and 88 which are in line with their respective irrigation passage 70 and vacuum passage 72 when the valves are in the depressed or actuated position, which is seen for valve plunger 80 in FIGS. 8 and 9. The valve plungers have shanks 90 and 92, which are of smaller diameter than the valve plunger and extend through openings in cover plate 94. The shank 92 is threaded and carries adjustable stop nut 96 thereon. Actuator buttons 98 and 100 are respectively mounted on the shanks 90 and 92 so that they are each individually rigidly engaged for digital actuation. Each of the shanks 90 and 92 has a slot therein on the lower side, and these slots are respectively engaged by pins 102 and 104. These pins prevent the valve plungers from rotating, and this is necessary because the cross bores 86 and 88 need to stay in alignment with the passages 70 and 72. This could be overcome by placing a groove around the spool rather than a hole through the plunger. However, the pins are also helpful in preventing the rotation of the valves because they are easier to manipulate when they do not rotate. In a surgical application, the ease and accuracy of manipulation are critically important.

In use, the endoscopic suction, irrigation and cautery instrument 20 is used in endoscopic surgery. Two sizes of cannula 38 are available. A cannula lumen with a 5 millimeter opening is satisfactory for normal suction and irrigation functions during endoscopic surgery. The fact that the cannula and body of the instrument are transparent now provides to the surgeon a completely see-through device. This enables the surgeon if there is something caught in one of the trumpet valve passages. The transparency is very helpful to permit the surgeon to see if a specimen of tissue has been caught in the valve body and elsewhere between the tip of the cannula and the suction valve. The cannula and valve body are now a window the surgeon can employ to see what is being withdrawn. This is helpful because, if the suction passage is not clear, at the end of suction, material may drip back into the operating field. On the other hand, if irrigation follows, the material left in the valve body and cannula would be sprayed back into the field. The clear cannula and clear instrument body eliminate this difficulty. When the smaller lumen is used, a suitable plug is provided in the threaded socket in the valve body which is not holding the cannula. Since both of the female threaded sockets 32 and 34 are the same, the cannula can be inserted into either end of the valve body, and the plug into the opposite end so that the instrument can be assembled for either a right- or a left-handed surgeon.

The instrument is also provided with an interchangeable cannula 38 which has a 10 millimeter outside diameter. This cannula is also clear so that, together with the clear valve body, the passage of suction material can be observed. The larger diameter cannula lumen permits the removal of larger material, such as clots and gallstones. In addition, the larger lumen permits the employment of a cautery electrode which extends through the larger suction and irrigation cannula 38. The installation of the cautery electrode 52 has been described previously. It can be advanced to the left or withdrawn to the right. It can be rotated by its adjusting wheel 58 so that the tip is oriented in the correct position. The cautery electrode 52 is preferably insulated over its length, except for its ends. When cautery is used, an electric current is applied by the tip of the electrode to the issue which is to be sealed. The electric charge causes capacitive coupling with any nearby conductive material. In the present instance, the cannula 38 is non-conductive so that it receives no charge. Use of the 10 millimeter cannula separates the surrounding tissue from the sides of the electrode so that there is little coupling. Thus, there is no capacitive coupling problem during the use of cautery through the sides of the cannula because it is non-conductive.

During laparoscopic surgery, there is a need to distend the patient's abdomen. Carbon dioxide is usually used. This is done to open space between the organs to permit passage of the laparoscope and endoscopic instruments and is called "insufflation" or "pneumoperitoneum." When a cautery electrode is used, it creates a considerable amount of smoke in this enclosed environment. The surgeon uses the suction function of the instrument to withdraw the smoke. However, if too much suction volume is employed, the entire pneumoperitoneum is withdrawn. The insufflation machine has a limited insufflation rate. Thus, it is desirable to control the suction rate. The adjustable stop 96 limits the downstroke of the valve 80 to limit the suction volume. Adjustment of the nut 96 adjusts this rate. The surgeon simply thumbs the adjustable stop nut 96 to the correct value to control the suction rate. The adjustable stop nut 96 is configured so that, when it is in its position of minimum suction flow, the suction rate is about 1½ liters per minute. In this way, the surgeon can maintain the suction and not be concerned about losing the space created by the pneumoperitoneum.

As described above, the removal of cap 48 permits complete withdrawal of the cautery electrode 52. It also permits the replacement with other cautery electrodes. The electrode 52 is standard for connection to a monopolar cable hookup. The wheel 58 provides for rotation and advancement retraction of the cautery electrode. The cautery electrode can be withdraw into the tip opening of the cannula and can be advanced and positioned by wheel 58 to stop the bleeding quickly and effectively without over-cauterizing surrounding tissues. After cauterization, the cautery electrode can be retracted. At the same time, when the cautery electrode positioned, the irrigation and suction can clear the field for accurate placement. The instrument can remove the excess blood, irrigate to find the source of bleeding, and film advance the cautery electrode to cauterize just what is bleeding. The withdrawal of the cautery electrode is important because, if the electrode remains extended, a cannula with an extended cautery electrode cannot be passed blindly around an organ to suction fluid behind or underneath the organ. Unexposed cautery tip on such a cannula would injure the organ or cause unreachable bleeding. Thus, with this combination of benefits, an advanced endoscopic suction, irrigation and cautery instrument is achieved.

This invention has been described in its presently contemplated best embodiment, and it is clear that it is susceptible to numerous modifications, modes and embodiments within the ability of those skilled in the art and without the exercise of the inventive faculty. Accordingly, the scope of this invention is defined by the scope of the following claims.

What is claimed is:

1. An endoscopic suction, irrigation and cautery instrument comprising:

a transparent valve body having two ends, a main passage in said valve body extending through said body from end to end, attachment means at each end of said passage;

a transparent tubular cannula detachably attached to said valve body at either of said attachment means on said valve body so that it may be attached at either end thereof, both said valve body and said cannula being made substantially transparent synthetic polymer composition material, said body having a suction connection thereon and having an irrigation connection thereon, passages in said body respectively connecting said suction passage to said main passage and said irrigation passage to said main passage; and a suction valve in said suction passage for controlling connection of said suction connection to said main passage, an irrigation valve in said irrigation passage for controlling connection of said irrigation connection to said main passage so that when suctioning, suction material can be observed through said cannula and through said valve body, said valve body being sized and said suction valve and irrigation valves being positioned so that said valve body can be held in the hand to position said cannula and the fingers of the same size can actuate said valve.

2. The instrument of claim 1 further including an adjustable stop connected to said suction valve to adjustably limit the open position of said suction valve to a position less than the maximum open position so as to control suction.

3. The instrument of claim 1 wherein said adjustable stop is accessible to the hand of the user which holds said valve body of said instrument.

4. The instrument of claim 3 wherein said adjustable stop is positioned to be finger-actuated by a person holding said valve body.

5. The instrument of claim 4 wherein each of said valves has an actuator button of different configuration so that said suction valve can be digitally distinguished from said irrigation valve.

6. The instrument of claim 1 further including a cautery electrode extending through said main passage in said body and through said cannula, said cautery electrode having finger control means thereon located to be positioned by a finger on the user's hand while the user holds said valve body in his hand.

7. An endoscopic suction, irrigation and cautery instrument comprising:

a valve body having a first end and a second end, a main passage through said valve body, said main passage having a first end and a second end respectively at the ends of said main body, first and second fastening means respectively at said first and second ends of said main passage, said valve body being made of substantially transparent synthetic polymer composition material;

a transparent dielectric cannula having fastening means thereon compatible with both said first and second fastening means for detachably securing sale cannula at one of said ends of said main body, said cannula terminating at a tip;

a cautery electrode passing through said main body from the end opposite said cannula and extending through said body and said cannula and terminating adjacent said tip of said cannula, said cautery electrode having a finger engageable surface for moving said cautery electrode with respect to said cannula, said cautery electrode having a first position wherein said tip of said cautery electrode is within said cannula and a second, extended position wherein said cautery tip is extended from said cannula; and connection means including finger operable valves for connecting suction and irrigation to said main passage so that actuation of said valves can cause irrigation and suction at said tip of said cannula and advancement of said cautery electrode can permit cauterization at said tip of said cannula.

8. The instrument of claim 7 further including attachment means for attaching said cautery electrode to said body, said attachment means including positioning stops which limits the position said cautery electrode between said first and second positions.

9. The instrument of claim 7 wherein finger engageable surface on said cautery electrode is an actuator thereon for manual grasp so that the user can advance, retract and rotate said cautery electrode.

10. The instrument of claim 9 wherein said suction valve and said irrigation valve are positioned in said valve body and actuators extend therefrom for finger actuation of said suction valve and said irrigation valve.

11. The instrument of claim 10 wherein said valve actuators are of different contours so that said suction valve can be distinguished by finger touch from said irrigation valve.

12. The instrument of claim 10 wherein said suction valve has an adjustable stop thereon to adjustably limit opening of said suction valve to less than full opening.

13. The instrument of claim 12 wherein said adjustable stop is positioned to be finger operable by the digital operator of said suction and irrigation valves.

14. The instrument of claim 7 wherein said cannula is interchangeable with cannula of other sizes, each of said cannula being substantially clear and dielectric.

15. The instrument of claim 7 wherein said attachment means on each end of said valve body are the same so that said cannula and said cautery electrode can be attached to either end of said valve body.

16. The instrument of claim 15 wherein said suction valve and said irrigation valve are positioned in said valve body and actuators extend therefrom for finger actuation of said suction valve and said irrigation valve.

17. An endoscopic suction, irrigation and cautery instrument comprising:

a valve body having a first end and a second end, a main passage through said valve body, said main passage having a first end and a second end respectively at the ends of said main body, first and second fastening means respectively at said first and second ends of said main passage;

a dielectric cannula having fastening means thereon compatible with both said first and second fastening means for detachably securing said cannula at one of said ends of said main body so that said cannula can be attached at either end of said main passage, said cannula terminating at a tip;

said body having a suction connection thereon and having an irrigation connection thereon, passages in said body respectively connecting said suction passage to said main passage and said irrigation passage to said main passage;

a suction valve in said suction passage for controlling connection of said suction connection to said main passage, said suction valve having an adjustable stop thereon to adjustably limit the opening of said suction valve to less than full opening so as to control the amount of suction in said cannula.

18. The instrument of claim 17 wherein said adjustable stop is positioned to be finger-operable by the operator of said suction and irrigation valves.

19. An endoscopic suction, irrigation and cautery instrument comprising:

a valve body having a first end and a second end, a main passage through said valve body, said main passage having a first end and a second end respectively at the ends of said main body, first and second fastening means respectively at said first and second ends of said main passage;

a dielectric cannula having fastening means thereon compatible with both said first and second fastening means for detachably securing said cannula at one of said ends of said main body so that said cannula can be selectively attached at either of said first or second ends of said main body;

a cautery electrode passing through said main body from the end opposite said cannula and extending through said body and said cannula and terminating adjacent said tip of said cannula, said cautery electrode having a finger engageable surface for moving said cautery electrode with respect to said cannula, said cautery electrode having finger-control means thereon located to be positioned by a finger on the user's hand while the user holds said valve body in his hand, said cautery electrode having a first position wherein said tip of said cautery electrode is within said cannula and a second, extended position wherein said cautery tip is extended from said cannula; and connection means including finger operable valves on said valve body for connecting suction and irrigation to said main passage so that actuation of said valves can cause irrigation and suction at said tip of said cannula and finger control of said cautery electrode can control the advancement of said cautery electrode and can permit cauterization at said tip of said cannula.

20. The instrument of claim 19 wherein said suction valve has an adjustable stop thereon to adjustably limit the opening of said suction valve to less than full opening, said adjustable stop being positioned so that it can be finger-operated by the operator of said suction and irrigation valves when he holds said valve body in his hands.

21. An endoscopic suction, irrigation and cautery instrument comprising:

a valve body having a first end and a second end, a main passage through said valve body, said main passage having a first end and a second end respectively at the ends of said main body;

a dielectric cannula detachably attached to said main body in line with said main passage therethrough, said cannula terminating at a tip;

connection means including finger-operable valves for connecting suction and irrigation to said main passage so that actuation of said valves can cause irrigation and suction at said tip of said cannula, said suction valve having an adjustable stop thereon to limit opening of said suction valve to less than full opening, said adjustable stop being positioned to be finger-operated by the operator of said suction and irrigation valves when he holds said valve body in his hand;

a cautery electrode passing through said main body and terminating adjacent said tip of said cannula, said cautery electrode having a finger engageable surface for moving said cautery electrode with respect to said cannula, said cautery electrode having a first position wherein said tip of said cautery electrode is within said cannula and a second, extended position wherein said cautery tip is extended from said cannula, said finger engageable surface of said cautery electrode being positioned to be finger engageable while the user holds said valve body in his hand.

22. The instrument of claim 21 wherein said attachment means on each end of said valve body are the same so that said cannula and said cautery electrode can be attached to either end of said valve body.

23. An endoscopic suction, irrigation and cautery instrument comprising:

a valve body having a first end and a second end, a main passage through said valve body, said main passage having a first end and a second end respectively at the ends of said main body, fastening means at least one of said ends of said main passage, said valve body being made of substantially transparent synthetic polymer composition material;

a transparent dielectric cannula having fastening means thereon compatible with said fastening means on said valve body for detachably securing said cannula at the end of said main body, said cannula terminating at a tip;

connection means including finger-operable valves for connecting suction and irrigation to said main passage so that actuation of said valves can cause irrigation and suction at said tip of said cannula, said suction valve having an adjustable stop thereon to adjustably limit opening of said suction valve to less than full opening, said adjustable stop being positioned to be finger-operable by the operator of said suction and irrigation valves while he holds said valve body in his hand.

* * * * *